(12) United States Patent
Ra et al.

(10) Patent No.: US 10,287,551 B2
(45) Date of Patent: May 14, 2019

(54) MEDIUM COMPOSITION FOR CULTURING STEM CELLS

(71) Applicant: R BIO CO., LTD., Seoul (KR)

(72) Inventors: Jeong Chan Ra, Chungcheongbuk-do (KR); Sung Keun Kang, Seoul (KR); Sung-Min Kim, Sejong-si (KR); Mi Sook Lee, Seoul (KR); Jin Hwa Lee, Gyeonggi-do (KR); Soon Ae Kwon, Gyeonggi-do (KR)

(73) Assignee: R BIO CO., LTD., Seoul (KR)

( * ) Notice: Subject to any disclaimer, the term of this patent is extended or adjusted under 35 U.S.C. 154(b) by 18 days.

(21) Appl. No.: 15/523,260

(22) PCT Filed: Oct. 28, 2015

(86) PCT No.: PCT/KR2015/011424
§ 371 (c)(1),
(2) Date: Apr. 28, 2017

(87) PCT Pub. No.: WO2016/068596
PCT Pub. Date: May 6, 2016

(65) Prior Publication Data
US 2017/0313986 A1  Nov. 2, 2017

(30) Foreign Application Priority Data

Oct. 29, 2014 (KR) .................. 10-2014-0148482
Dec. 26, 2014 (KR) .................. 10-2014-0190671

(51) Int. Cl.
*C12N 5/0775* (2010.01)

(52) U.S. Cl.
CPC ........ *C12N 5/0667* (2013.01); *C12N 2500/05* (2013.01); *C12N 2500/14* (2013.01); *C12N 2500/30* (2013.01); *C12N 2500/32* (2013.01); *C12N 2500/38* (2013.01); *C12N 2500/84* (2013.01); *C12N 2500/99* (2013.01); *C12N 2501/115* (2013.01); *C12N 2501/30* (2013.01); *C12N 2501/33* (2013.01); *C12N 2501/39* (2013.01)

(58) Field of Classification Search
None
See application file for complete search history.

(56) References Cited

U.S. PATENT DOCUMENTS 8,871,513 B2 * 10/2014 Ra ...................... C12N 5/0605
                                                         435/325

FOREIGN PATENT DOCUMENTS

| JP | 2010252778 A | 11/2010 |
|---|---|---|
| KR | 10-0679642 B1 | 2/2007 |
| KR | 10-0795708 B1 | 1/2008 |
| KR | 10-0818214 B1 | 4/2008 |
| KR | 10-2012-0008223 A | 1/2012 |
| KR | 10-2013-0117343 A | 10/2013 |
| KR | 10-2014-0000945 A | 1/2014 |
| KR | 10-2014-0081762 A | 7/2014 |
| WO | 2006019357 A1 | 2/2006 |
| WO | WO-2012008813 A2 * | 1/2012 ........... C12N 5/0605 |
| WO | WO2014141392 A1 | 9/2014 |

OTHER PUBLICATIONS

Hass, Ralf; et al; "Different populations and sources of human mesenchymal stem cells (MSC): A comparison of adult and neonatal tissue-derived MSC" Cell Communication & Signaling, 9, 1-14, 2011 (Year: 2011).*

Ayatollahi, M., et al., "Conditions to improve expansion of human mesenchymal stem cells based on rat samples", "World Journal of Stem Cells", Jan. 26, 2012, pp. 1-8, vol. 4, No. 1.

Pal, R., et al., "Phenotypic and functional comparison of optimum culture conditions for upscaling of bone marrow-derived mesenchymal stem cells", "Journal of Tissue Engineering and Regenerative Medicine", Feb. 19, 2009, pp. 163-174, vol. 3, No. 3.

Ra, J., et al., "Safey of Intravenous Infusion of Human Adipose Tissue-Derived Mesenchymal Stem Cells in Animals and Humans", "Stem Cells and Development", Feb. 8, 2011, pp. 1297-1308, vol. 20, No. 8.

GIBCO Life Technologies, "Defined Keratinocyte-SFM (1X), Liquid", "https://www.thermofisher.com/order/catalog/product/10744019?SID=srch-srp-10744019", Jul. 15, 2014, p. 2 No. MAN0007310, Publisher: GIBCO Life Technologies.

Ma, J., et al., "Concise Review: Cell-Based Strategies in Bone Tissue Engineering and Regenerative Medicine", "Stem Cells Translational Medicine", 2014, pp. 98-107, vol. 3.

Tsai, D., et al., "Glucose Effect of Pre-Differentiation Culture on Chondrogenesis of Human Mesenchymal Stem Cells", "56th Annual Meeting of the Orthopaedic Research Society", 2010, p. 2, No. Poster No. 763.

* cited by examiner

Primary Examiner — David W Berke-Schlessel
(74) Attorney, Agent, or Firm — Hultquist, PLLC; Steven J. Hultquist (57) ABSTRACT

The present disclosure relates to a medium composition for culturing stem cells, and more specifically, to a medium composition for culturing mesenchymal stem cells, in which the medium composition includes a basic medium in which various quasi-completed mediums (DMEM, α-MEM, IMDM, F12, and DMEM/F12) are mixed, L-ascorbic acid 2-phosphate, fetal bovine serum, basic fibroblast growth factors (b-FGF), insulin, N-acetyl-L-cysteine, calcium chloride, and hydrocortisone.

According to the present disclosure, it is capable of improving proliferation ability and differentiation ability of the mesenchymal stem cells, and is capable of producing cell therapy products more economically using the mesenchymal stem cells by enabling the mesenchymal stem cells to be cultured at a low price compared to the existing culturing methods.

8 Claims, 11 Drawing Sheets

(6 of 11 Drawing Sheet(s) Filed in Color)

ium composition for culturing stem cells, and more specifically, to a medium composition for culturing mesenchymal stem cells, in which the medium composition includes a basic medium in which various quasi-completed mediums (DMEM, α-MEM, IMDM, F12, and DMEM/F12) and Defined Keratinocyte-SFM are mixed, L-ascorbic acid 2-phosphate, fetal bovine serum, basic fibroblast growth factors (b-FGF), insulin, N-acetyl-L-cysteine, calcium chloride, and hydrocortisone.

MEDIUM COMPOSITION FOR CULTURING STEM CELLS

CROSS-REFERENCE TO RELATED APPLICATIONS

This application is a U.S. national phase under the provisions of 35 U.S.C. § 371 of International Patent Application No. PCT/KR2015/011424 filed Oct. 28, 2015, which in turn claims priority of Korean Patent Application No. 10-2014-0148482 filed Oct. 29, 2014 and Korean Patent Application No. 10-2014-0190671 filed Dec. 26, 2014. The disclosures of such international patent application and Korean priority patent applications are hereby incorporated herein by reference in their respective entireties, for all purposes.

BACKGROUND

Field

The present disclosure relates to a medium composition for culturing stem cells, and more specifically, to a medium composition for culturing mesenchymal stem cells, in which the medium composition includes a basic medium in which various quasi-completed mediums (DMEM, α-MEM, IMDM, F12, and DMEM/F12) and Defined Keratinocyte-SFM are mixed, L-ascorbic acid 2-phosphate, fetal bovine serum, basic fibroblast growth factors (b-FGF), insulin, N-acetyl-L-cysteine, calcium chloride, and hydrocortisone.

Description of the Related Art

Cells that have the ability to differentiate into two or more cells while maintaining self-replicating ability are called stem cells. Stem cells may be broadly divided into totipotent stem cells, pluripotent stem cells, and multipotent stem cells, which can be differentiated into only specific cells in tissues and organs. As stem cells, adult stem cells is a generic concept of cells, which are involved in the function of inducing the development of tissues and organs of the fetal stage, neonatal stage and adult stage, maintenance of adult tissue homeostasis and regeneration of tissue damage.

Recently, adult stem cells have been attracting attention in the development research of new regenerative medical treatment techniques such as regeneration and function restoration of biological tissues and organs that are dysfunctional or incompatible with various diseases or accidents. In addition, the development research of treatment techniques using stem cells will lead to a greater utilization of stem cells, as the development of cell-tissue replacement therapy methods is predicted beyond the conventional classical drug therapy or surgical treatment methods.

Accordingly, various functions of stem cells have been studied at present. Among them, cell therapy techniques using mesenchymal stem cells begin gaining the spotlight and techniques for the improvement to be suitable for being treated by means of mesenchymal stem cells separated from human body are being developed (WO 2006/019357, Korean Patent Registration No. 0795708, and Korean Patent Registration No. 0818214).

Currently, the research and development process related to cell therapy products using adult stem cells is progressed through a sequence of processes that are introduced into the patient's own body by inducing cell proliferation and/or differentiation through in vitro culture after collecting stem cells, blood-derived mononuclear cells or bone marrow-derived mononuclear cells from a patient, and inducing the undifferentiation (stem cells and/or precursor cells) and/or the implantation of differentiated cells. However, the mesenchymal stem cell culture medium, which is currently used and is most optimized for stem cell-sustaining ability (stemness) of the mesenchymal stem cell, high division ability, and compact morphology retention, is a financial burden in research of stem cell therapy products due to high costs (Korean Patent Registration No. 0795708).

In this regard, the present inventors did their best to develop a medium for stem cell culture that can reduce the production cost of mesenchymal stem cells and further enhance the culture efficiency. As a result, the present inventors have developed a mixed medium in which commonly uses a KSFM-P medium with a high cost and high efficiency that is currently used for culturing stem cells and relatively inexpensive quasi-completed product medium or a finished product stem cell culture medium are mixed at a certain ratio. In addition, as a result of culturing mesenchymal stem cells by using the mixed medium, the inventors confirmed that the culture efficiency of stem cells is increased, and completed the present disclosure.

SUMMARY

It is an object of the present disclosure to provide an economical medium composition for culturing stem cells which is capable of maintaining the differentiation ability while having high proliferation ability.

It is another object of the present disclosure to provide a method for culturing mesenchymal stem cells using the medium composition.

In order to achieve the above objects, the present disclosure provides a medium composition for culturing mesenchymal stem cells that contains a basic medium in which mediums selected from the group consisting of DMEM, α-MEM, IMDM, F12, and DMEM/F12 and Defined Keratinocyte-SFM are mixed, L-ascorbic acid 2-phosphate, fetal bovine serum, basic fibroblast growth factors (b-FGF), insulin, N-acetyl-L-cysteine, calcium chloride, and hydrocortisone.

The present disclosure also provides a method for culturing mesenchymal stem cells, in which the mesenchymal stem cells are cultured in the medium composition.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENT

Unless otherwise defined, all technical and scientific terms used in the present specification have the same meanings as commonly understood by a skilled expert in the technical field to which the present disclosure belongs. Generally, the nomenclature used in the present specification and experimental methods described hereinafter are well known and is commonly used in the present technical field.

In the present disclosure, it was confirmed that when adipose-derived mesenchymal stem cells were cultured in an environment that 5% FBS was added to each medium in which a KSFM-P medium (Korean Patent Registration No. 0679642) which has been used in culturing the conventional mesenchymal stem cells and DMEM (Dulbeco's Modified Eagle's Medium), IMDM (Iscove's Modified Dulbecco's Medium), α-MEM (Alpha Modification of Eagle's Medium), F12 (Nutrient Mixture F-12), and DMEM/F12 (Dulbecco's Modified Eagle Medium: Nutrient Mixture F-12) medium, which can be purchased relatively inexpensively in the form of a quasi-finished product, are mixed, there was almost no change in the characteristics of the stem cells, and that the size of the cells could be maintained constantly while the cells were proliferated effectively.

Accordingly, in one aspect, the present disclosure relates to a medium composition for culturing mesenchymal stem cells that contains a basic medium in which mediums selected from the group consisting of DMEM, α-MEM, IMDM, F12, and DMEM/F12 and Defined Keratinocyte-SFM are mixed, L-ascorbic acid 2-phosphate, fetal bovine serum, basic fibroblast growth factors (b-FGF), insulin, N-acetyl-L-cysteine, calcium chloride, and hydrocortisone.

The term "stem cells" used in the present disclosure refer to a cell having the self-replicating ability and the ability to differentiate into two or more cells, and "adult stem cells" refer to a stem cell shown in the stage where each organ of embryos is formed as a generation process is progressed or in the adult stage.

The term "mesenchymal stem cells" used in the present disclosure refer to undifferentiated stem cells isolated from human or mammalian tissues and may be derived from various tissues. In particular, they may be umbilical cord-derived mesenchymal stem cells, cord blood-derived mesenchymal stem cells, bone marrow-derived mesenchymal stem cells, adipose-derived mesenchymal stem cells, muscle-derived mesenchymal stem cells, nerve-derived mesenchymal stem cells, skin-derived mesenchymal stem cells, amniotic membrane-derived mesenchymal stem cells, and placenta-derived mesenchymal stem cells. Techniques for isolating stem cells from each tissue are already known in the pertinent art.

The term "adipose-derived stem cells" used in the present disclosure refer to an undifferentiated stem cell isolated from adipose tissue, and its isolation method may be, for example, as follows. That is, after culturing a fat-containing suspension suspended in physiological saline obtained from liposuction, the stem cell layer adhered to the culture container such as a flask is treated with trypsin and then is collected, or the adipose-derived stem cells may be isolated through a method of directly collecting that suspended in a small amount of physiological saline by scrapping them off by a scraper.

In the present disclosure, the medium is characterized by containing 0.05 to 1 mM of ascorbic acid 2-phosphate, 2 to 20% fetal bovine serum, 10 to 1 ng/ml of basic fibroblast growth factor (b-FGF), 0.1 to 100 μg/ml of insulin, 0.2 to 20 mM N-acetyl-L-cysteine, 0.01 to 1 mM of calcium chloride and 5 ng/ml to 1 μg/ml of hydrocortisone.

In the present disclosure, the mixture ratio of the quasi-completed mediums DMEM (Dulbecco's Modified Eagle's Medium), IMDM (Iscove's Modified Dulbecco's Medium), α-MEM (Alpha Modification of Eagle's Medium), F12 (Nutrient Mixture F-12), and DMEM/F12 (Dulbecco's Modified Eagle's Medium; Nutrient Mixture F-12) mediums to Defined Keratinocyte-SFM medium is preferably 1:0.1 to 10, more preferably 1:0.25 to 3.

In one embodiment of the present disclosure, when the mixed medium in which the quasi-completed mediums, DMEM, IMDM, α-MEM, F12, and DMEM/F12 mediums and a KSFM-P medium are mixed at a ratio of 1:0.5; 1:1, 1:2, 1:3, and 1:4 is used, it may obtain a similar cell form as the case of culturing it by using a KSFM-P single medium, and shows a remarkably excellent cell yield than the case of using the KSFM-P single medium.

In another aspect, the present disclosure relates to a method for culturing mesenchymal stem cells, in which the method includes culturing mesenchymal stem cells in the medium composition.

In the present disclosure, the mesenchymal stem cells may be characterized in that they are derived from human adipose.

Hereinafter, the present disclosure will be described in more detail by way of examples. It will be apparent to a person having ordinary skill in the pertinent art that these embodiments are for illustrative purposes only and that the scope of the present disclosure is not construed as being limited by these examples.

Example 1: Isolation of Human Adipose Tissue-Derived Mesenchymal Stem Cells

Human adipose tissue obtained from abdominal fat was isolated by liposuction and washed with PBS. The tissue was finely cut and digested with DMEM mediums adding collagenase type 1 (1 mg/ml) at 37° C. for 2 hours. After being washed with PBS, it was centrifuged at 1000 rpm for 5 minutes. The supernatant was suctioned and the pellet remaining on the bottom was washed with PBS and then centrifuged at 1000 rpm for 5 minutes. After removing debris by filtering them in 100 μm mesh, the cells were washed with PBS, and then they were cultured in a DMEM (10% FBS, 2 mM NAC, and 0.2 mM ascorbic acid) medium.

After one night, the unadhered cells were washed with PBS, and Keratinocyte-SFM mediums containing 5% FBS, 2 mM NAC, 0.2 mM ascorbic acid, 0.09 mM calcium, 5 ng/ml rEGF, 5 μg/ml insulin and 74 ng/ml Hydrocortisone were replaced every 2 days and sub-cultured to prepare four successive multipotent mesenchymal stem cells derived from adipose tissue.

Example 2: Culture of Human Adipose Tissue-Derived Mesenchymal Stem Cells in a Mixed Medium The cells were cultured in the medium alone or in a mixed medium, that is, KSFM-P (Table 1) and quasi-completed mediums, DMEM (Dulbecco's Modified Eagle's Medium), IMDM (Iscove's Modified Dulbecco's Medium, Gibco, BRL), α-MEM (Alpha Modification of Eagle's Medium, Gibco, BRL), F12 (Nutrient Mixture F-12, Gibco, BRL), and DMEM/F12 (Dulbecco's Modified Eagle Medium: Nutrient Mixture F-12, Gibco, BRL), and the adhesion ability, density, form and yield, etc. of stem cells were confirmed.

TABLE 1

The components of the KSFM-P medium used in the present disclosure

| Component | available from | Concentration |
| --- | --- | --- |
| Defined Keratinocyte-SFM | Invitrogen | |
| L-ascorbic acid 2-phosphate | Sigma-aldrich | 0.2 mM |
| Insulin | Millipore | 5 μg/ml |
| N-acetyl-L-cysteine | Sigma-aldrich | 2 mM |
| Calcium chloride | Sigma-aldrich | 0.09 mM |
| Hydrocortisone | Sigma-aldrich | 74 ng/ml |
| Fetal Bovine Serum | Invitrogen | 5% |

(1) When DMEM was Used as a Quasi-Completed Medium
① KSFM-P (10% FBS)
② DMEM (10% FBS)
③ DMEM (10% FBS)+KSFM-P (10% FBS); Mixture ratio 1:1
④ DMEM (10% FBS)+KSFM-P (10% FBS); Mixture ratio 1:2
⑤ DMEM (10% FBS)+KSFM-P (10% FBS); Mixture ratio 1:3
⑥ DMEM (10% FBS)+KSFM-P (10% FBS); Mixture ratio 1:4
⑦ DMEM (10% FBS)+KSFM-P (10% FBS); Mixture ratio 2:1

$1 \times 10^4$ cells/well of adipose-derived mesenchymal stem cells of P4 were inoculated on a 6-well plate containing each medium, and were cultured for a total of 5 days, and the morphology of the stem cells was measured for 2 days and 5 days, respectively. Five days after the culture, the cultured stem cells were washed with DPBS, and 200 μl of TriPLE solution was added thereto, followed by reaction at 37° C. for 5 minutes in a culture medium to desorb the cells. 800 μl of DMEM (10% FBS) was added to each well to neutralize the TriPLE solution, transferred to a sterile 1.5 ml EP tube, and centrifuged at 800 rpm for 3 minutes. After centrifugation, the supernatant was removed and 500 ml of DPBS was added to re-suspend the isolated cells. DPBS in which 10 μl of cells are suspended and 10 μl of trypan blue were mixed and the cell number, survival rate and cell size were measured.

(2) When Using α-MEM, IMDM, F12, and DMEM/F12 as a Quasi-Completed Medium
① KSFM-P (5% FBS)
② Quasi-completed medium (5% FBS)
③ Quasi-completed medium (5% FBS)+KSFM-P (5% FBS); Mixture ratio 1:1
④ Quasi-completed medium (5% FBS)+KSFM-P (5% FBS); Mixture ratio 1:2
⑤ Quasi-completed medium (5% FBS)+KSFM-P (5% FBS); Mixture ratio 1:3
⑥ Quasi-completed medium (5% FBS)+KSFM-P (5% FBS); Mixture ratio 2:1
⑦ Quasi-completed medium (5% FBS)+KSFM-P (5% FBS); Mixture ratio 3:1

$3 \times 10^5$ cells/well of adipose-derived mesenchymal stem cells of P4 were inoculated on a T75 plate containing each medium and cultured until 90% density was observed, and the morphology of each stem cell was measured. Five days after the culture, the cultured stem cells were washed with DPBS, and 200 μl of TriPLE solution was added thereto, followed by reaction at 37° C. for 5 minutes in a culture medium to desorb the cells. 800 μl of DMEM (10% FBS) was added to each well to neutralize the TriPLE solution, transferred to a sterile 1.5 ml EP tube, and centrifuged at 800 rpm for 3 minutes. After centrifugation, the supernatant was removed and 500 ml of DPBS was added to re-suspend the isolated cells. 10 μl of cells suspended in DPBS and 10 μl of trypan blue were mixed and the cell number, survival rate and cell size were measured.

(1) Morphology of Stem Cells

Figure 1:
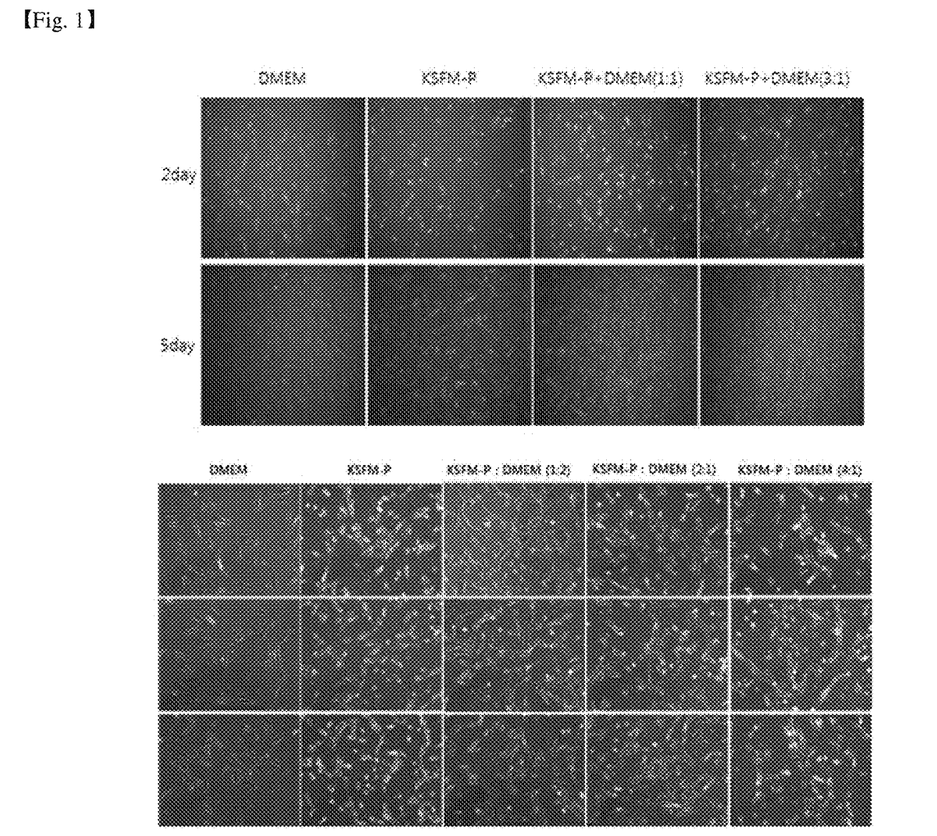
FIG. 1 illustrates morphological changes of adipose-derived mesenchymal stem cells in a mixed medium with DMEM, which is a quasi-completed medium.
Figure 2:
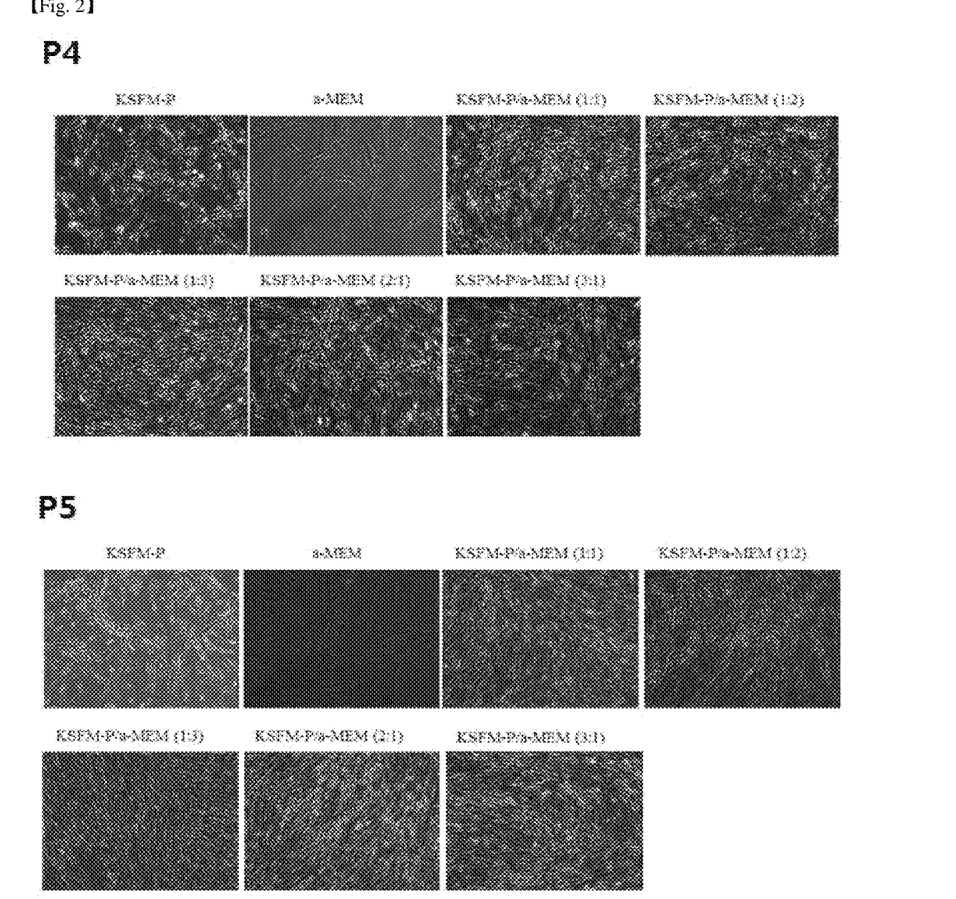
FIG. 2 illustrates morphological changes of adipose-derived mesenchymal stem cells in a mixed medium with α-MEM, which is a quasi-completed medium.
Figure 3:
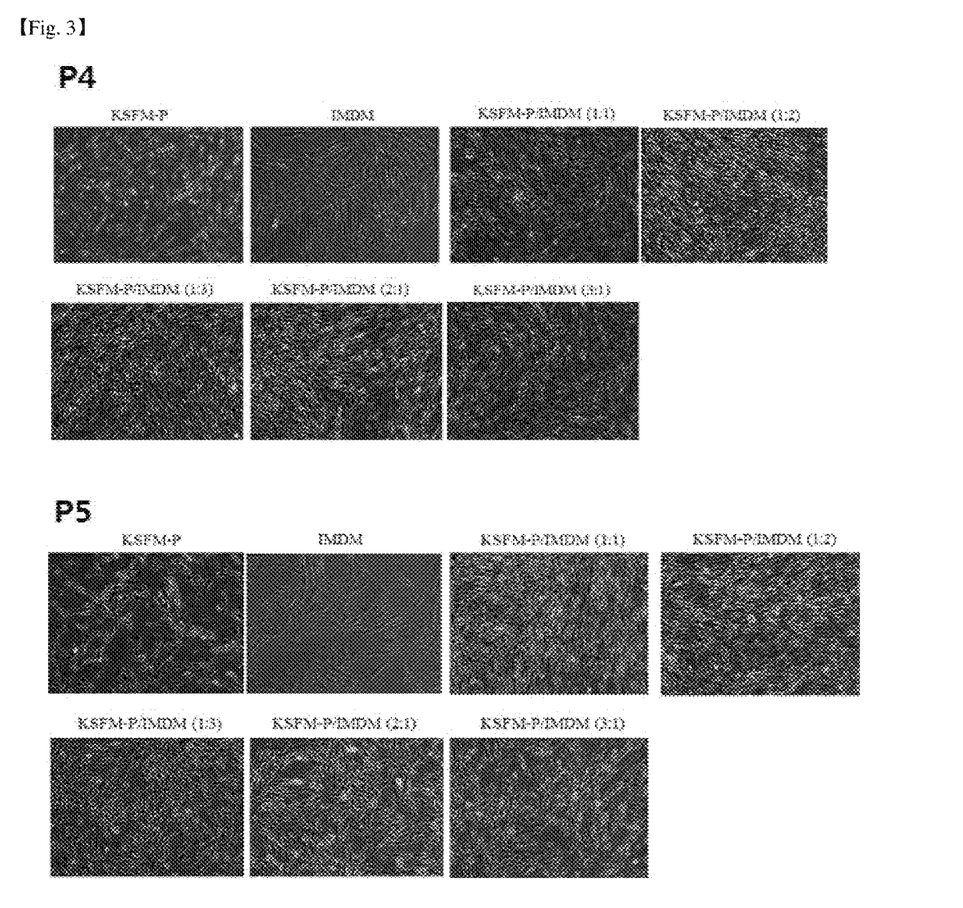
FIG. 3 illustrates morphological changes of adipose-derived mesenchymal stem cells in a mixed medium with IMDM, which is a quasi-completed medium.
Figure 4:
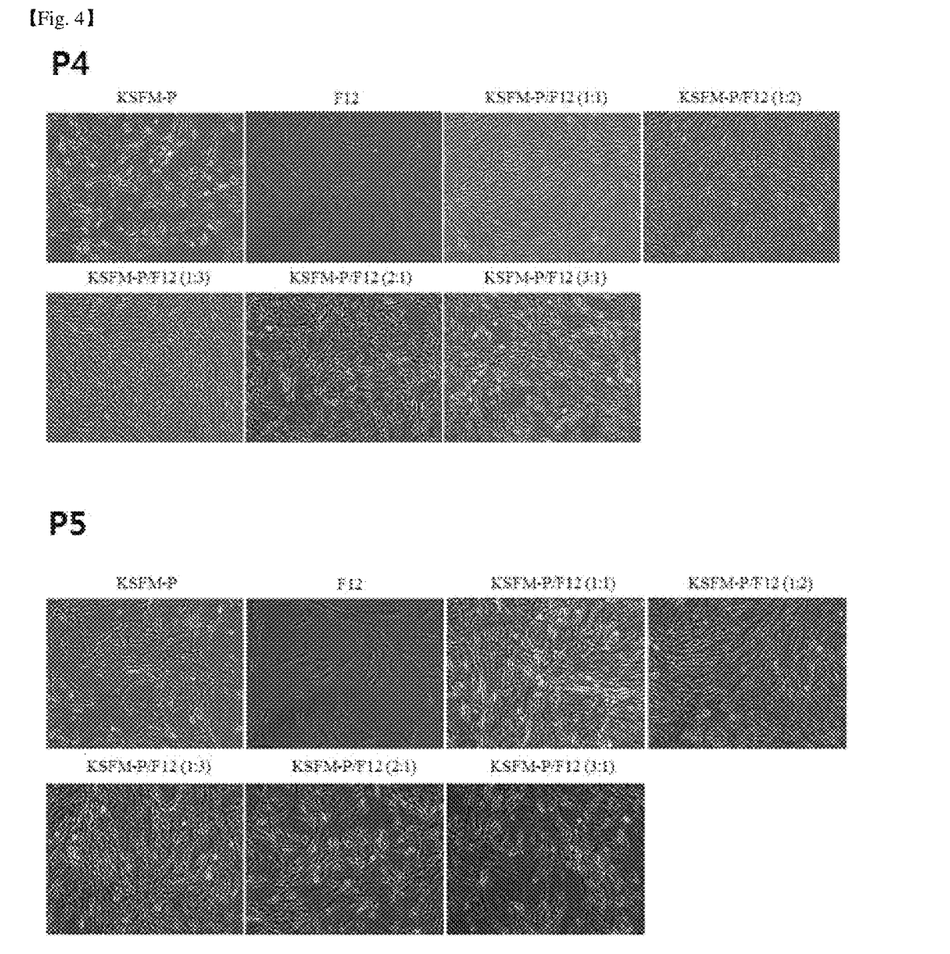
FIG. 4 illustrates morphological changes of adipose-derived mesenchymal stem cells in a mixed medium with F12, which is a quasi-completed medium.
Figure 5:
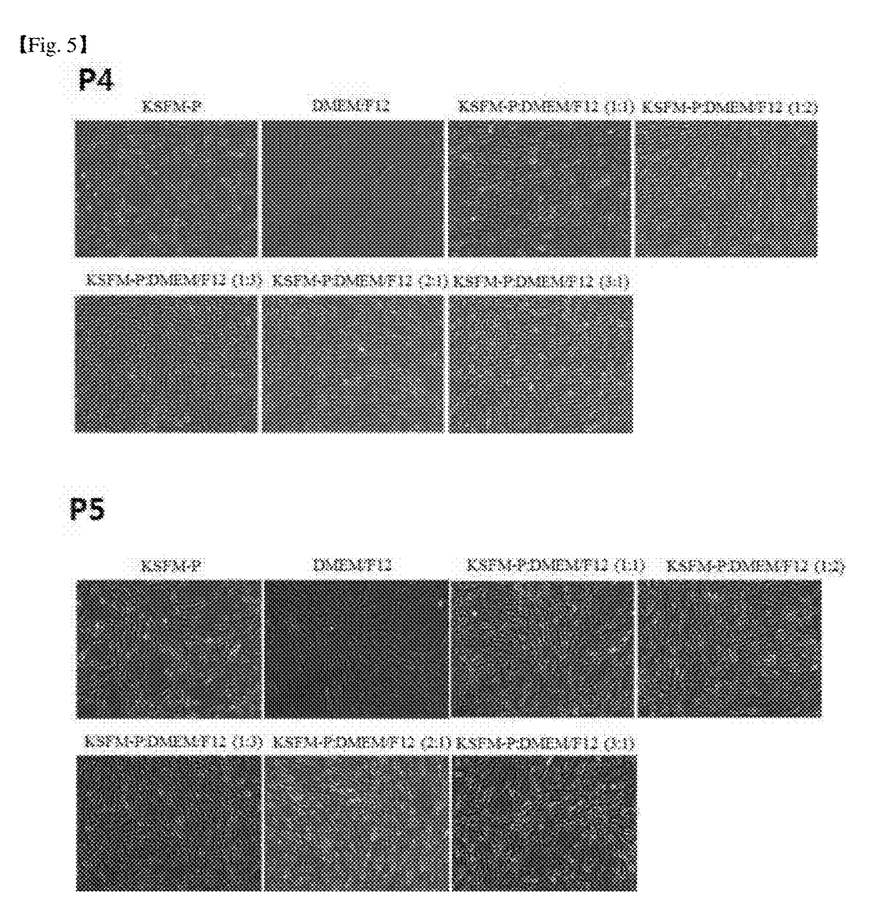
FIG. 5 illustrates morphological changes of adipose-derived mesenchymal stem cells in a mixed medium with DMEM/F12, which is a quasi-completed medium.
Figure 6:
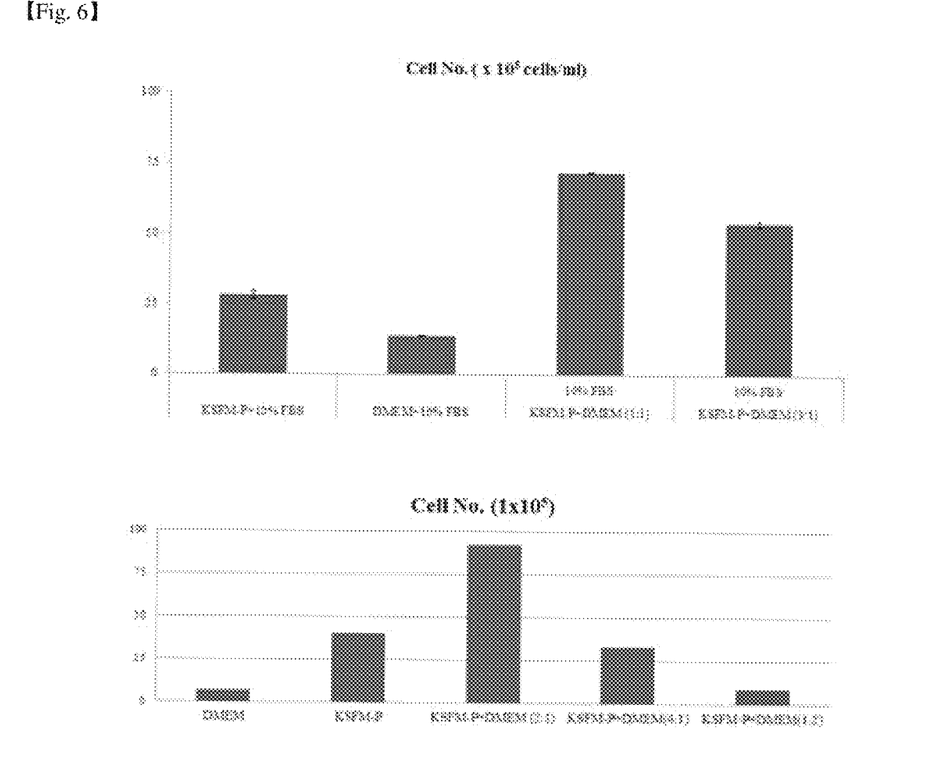
FIG. 6 illustrates the cell yield of adipose-derived mesenchymal stem cells in a mixed medium with DMEM, which is a quasi-completed medium.
Figure 7:
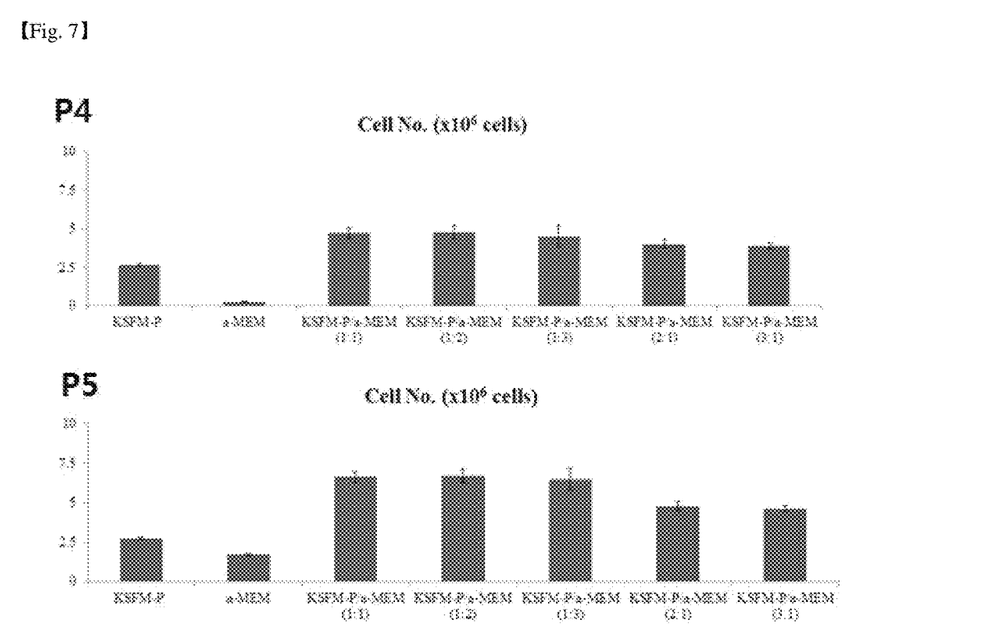
FIG. 7 illustrates the cell yield of adipose-derived mesenchymal stem cells in a mixed medium with α-MEM, which is a quasi-completed medium.
Figure 8:
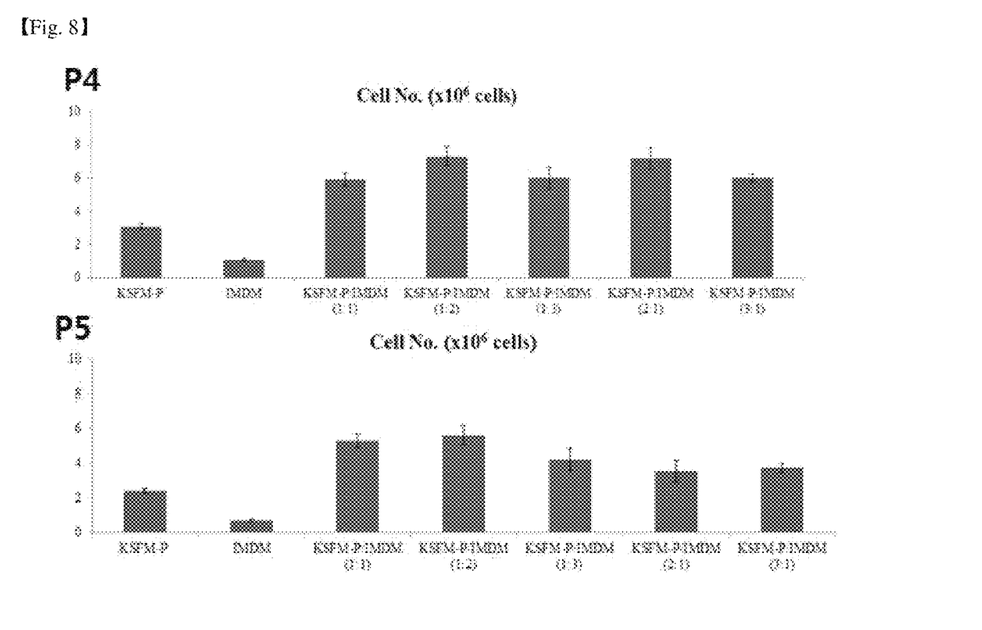
FIG. 8 illustrates the cell yield of adipose-derived mesenchymal stem cells in a mixed medium with IMDM, which is a quasi-completed medium.
Figure 9:
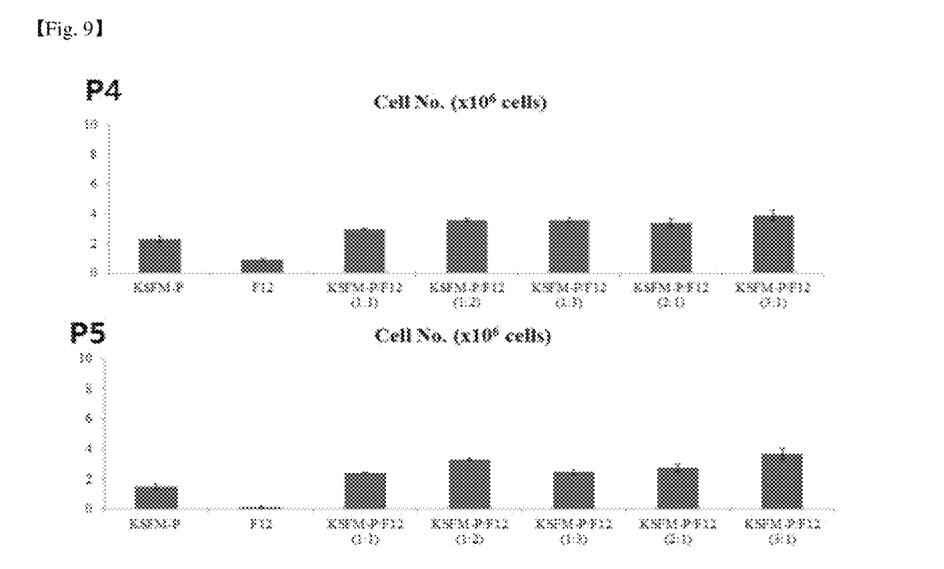
FIG. 9 illustrates the cell yield of adipose-derived mesenchymal stem cells in a mixed medium with F12, which is a quasi-completed medium.
Figure 10:
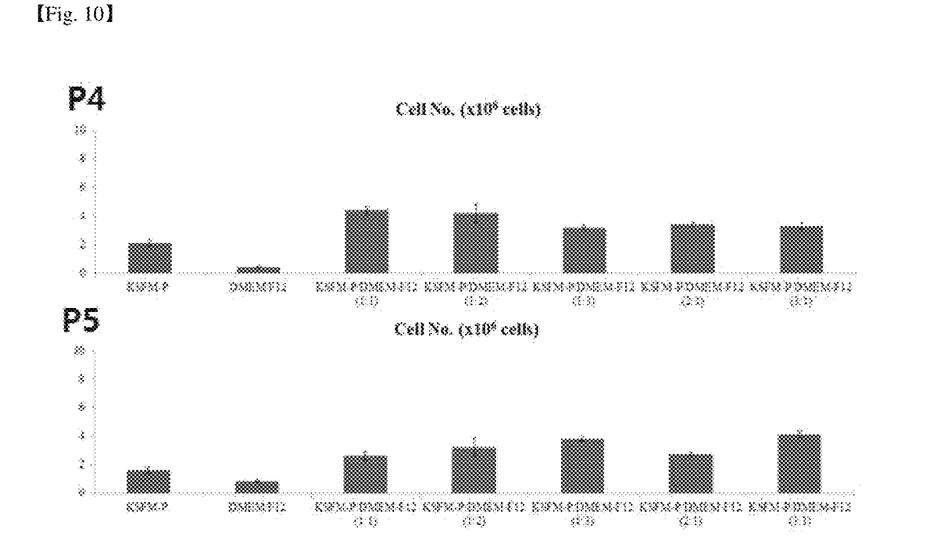
FIG. 10 illustrates the cell yield of adipose-derived mesenchymal stem cells in a mixed medium with DMEM/F12, which is a quasi-completed medium.

Changes in cell morphology during culture in each medium were photographed during the culture and observed. As a result, as shown in FIG. 1, it was confirmed that the initial adhesion ability (2 days in culture) of the cells was excellent in the groups (Group 3 and 4) in which two culture mediums were mixed as compared to KSFM-P or DMEM medium. As shown in FIGS. 2 to 5, it was confirmed that the cell proliferation ability was excellent in the groups (Groups 3 to 7) in which two culture mediums were mixed as compared to KSFM-P or each quasi-completed medium.

As to the morphology of the cells, the cells cultured in each quasi-completed medium is shown to have a relatively large and elongated form in terms of the size of cells as compared to the cells cultured in the other groups of mediums, and in the other groups, they are similar to the cells cultured in a KSFM-P medium. In contrast, it was confirmed that the density of cells was significantly increased when cultured in the mixed medium, compared to when cultured in the KSFM-P or each of the quasi-completed medium and a single medium. Accordingly, it was confirmed that a mixed medium mixing KSFM-P and a quasi-completed medium was more effective for cell size and growth.

(2) Yield of Stem Cells (Number) and Cell Size (Size)

The adipose-derived mesenchymal stem cells were cultured for 5 days in each medium, and then the stem cells were collected using TriPLE solution and the number was measured by using trypan blue technique.

As to the size of the cultured adipose-derived stem cells, the average size of the cells was set by using a Luna™ automated cell counter (Logos Biosystems, Inc. USA) after stem cells were obtained.

Figure 11:
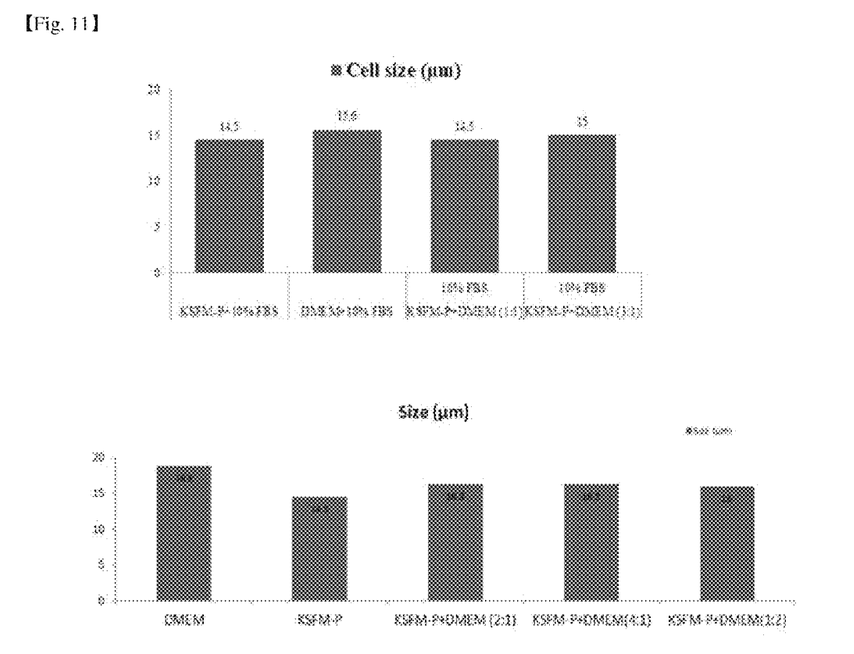
FIG. 11 illustrates changes in a cell size after culturing adipose-derived mesenchymal stem cells in a mixed medium with DMEM, which is a quasi-completed medium.
Figure 12:
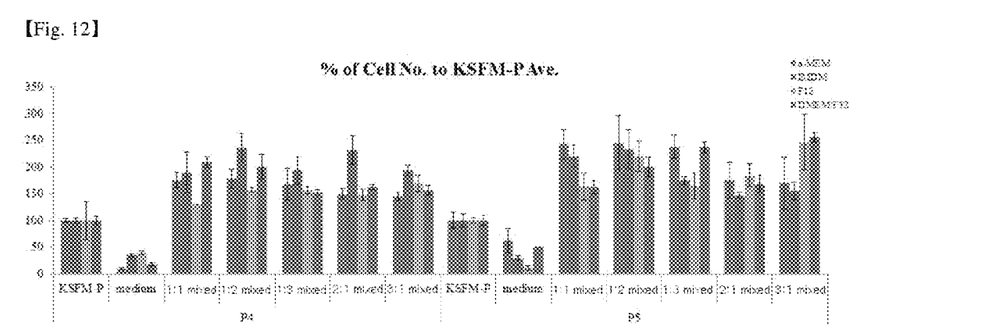
FIG. 12 is a graph showing the cell yield of adipose-derived mesenchymal stem cells in each mixed medium, in which the cell yield is expressed as a percentage with respect to the cell yield in a KSFM-P medium.

The results are shown in Tables 2 to 4 and FIG. 11.

As a result, as shown in Tables 2 to 4, the cell yield in the KSFM-P medium, which is a medium with the stem cell optimum condition, increased about twice as much as that of the quasi-completed medium. In addition, it was confirmed that the KSFM-P medium is suitable as compared to the quasi-completed medium in culturing stem cells.

In addition, as a result of culturing stem cells in a culture medium in which a KSFM-P culture medium and a quasi-completed medium were mixed at a certain ratio, it was confirmed that the cell yield was significantly increased by 2-3 times than the number of cells collected in a KSFM-P medium.

In addition, when the stem cell proliferation ability of the KSFM-P culture medium and each of the mixed mediums was compared, it was confirmed that when the IMDM medium, which is a quasi-completed medium, is mixed, it exhibited significantly high cell yield than the stem cells cultured in the other mediums.

Thus, it can be understood that by mixing the KSFM-P medium with the quasi-completed medium, the culture conditions necessary for cell growth are more effective than the KSFM-P culture medium alone.

As a result, as shown in Tables 2 and 3, the size of the stem cells cultured in each culture medium showed an average of about 15 to 17 μm with no significant difference. In other words, it can be understood that each culture medium had no significant effect on the cell size when it was obtained differently from the characteristics of cells seen with the naked eye.

TABLE 2

Stem cell yield in mixed mediums

| Culture condition | Cell No. ($\times 10^5$ cells/ml) |
|---|---|
| KSFM-P + 10% FBS | 28 |
| DMEM + 10% FBS | 13.8 |
| KSFM-P + DMEM (1:1) 10% FBS | 72 |
| KSFM-P + DMEM (3:1) 10% FBS | 54 |
| KSFM-P + 10% FBS | 40 |
| DMEM + 10% FBS | 6.5 |
| KSFM-P + DMEM (2:1) 10% FBS | 92 |
| KSFM-P + DMEM (4:1) 10% FBS | 33 |
| KSFM-P + DMEM (1:2) 10% FBS | 8.7 |

TABLE 3

Stem cell size in mixed mediums

| Culture condition | | Cell size (μm) |
|---|---|---|
| KSFM-P + 10% FBS | | 14.5 |
| DMEM + 10% FBS | | 15.6 |
| KSFM-P + DMEM (1:1) | 10% FBS | 14.5 |
| KSFM-P + DMEM (3:1) | 10% FBS | 15 |
| KSFM-P + 10% FBS | | 14.5 |
| DMEM + 10% FBS | | 18.9 |
| KSFM-P + DMEM (2:1) | 10% FBS | 16.3 |
| KSFM-P + DMEM (4:1) | 10% FBS | 16.3 |
| KSFM-P + DMEM (1:2) | 10% FBS | 16 |

TABLE 4

1. α-MEM mixed mediums

| P4 | Number of cells ($\times 10^6$) | Survival Rate (%) | Size (μm) |
|---|---|---|---|
| KSFM-P-P | 2.69 | 96 | 15.3 |
| a-MEM | 0.25 | 85.7 | 18.2 |
| KSFM-P-P/a-MEM (1:1) | 4.73 | 97.4 | 16.3 |
| KSFM-P-P/a-MEM (1:2) | 4.8 | 97.2 | 16.3 |
| KSFM-P-P/a-MEM (1:3) | 4.53 | 96.6 | 16.7 |
| KSFM-P-P/a-MEM (2:1) | 4.03 | 95.7 | 16.7 |
| KSFM-P-P/a-MEM (3:1) | 3.9 | 95.6 | 17.6 |

| P5 | Number of cells ($\times 10^6$) | Survival Rate (%) | Size (μm) |
|---|---|---|---|
| KSFM-P-P | 2.73 | 92.9 | 15.8 |
| a-MEM | 1.7 | 96.3 | 21.95 |
| KSFM-P-P/a-MEM (1:1) | 6.63 | 97.7 | 16.3 |
| KSFM-P-P/a-MEM (1:2) | 6.7 | 98 | 16.4 |
| KSFM-P-P/a-MEM (1:3) | 6.5 | 96.8 | 16.8 |
| KSFM-P-P/a-MEM (2:1) | 4.8 | 97 | 18.3 |
| KSFM-P-P/a-MEM (3:1) | 4.63 | 95.6 | 18.7 |

2. IMDM mixed mediums

| P4 | Number of cells ($\times 10^6$) | Survival Rate (%) | Size (μm) |
|---|---|---|---|
| KSFM-P-P | 3.10 | 93.1 | 15.3 |
| IMDM | 1.07 | 92.1 | 20.3 |
| KSFM-P-P/IMDM (1:1) | 5.90 | 98.03 | 17.6 |
| KSFM-P-P/IMDM (1:2) | 7.30 | 97.5 | 17.5 |
| KSFM-P-P/IMDM (1:3) | 6.00 | 97.96 | 15.9 |
| KSFM-P-P/IMDM (2:1) | 7.20 | 96.53 | 15.2 |
| KSFM-P-P/IMDM (3:1) | 6.00 | 99 | 15.4 |

| P5 | Number of cells ($\times 10^6$) | Survival Rate (%) | Size (μm) |
|---|---|---|---|
| KSFM-P-P | 2.4 | 96.5 | 16.2 |
| IMDM | 0.71 | 96.5 | 20.5 |
| KSFM-P-P/IMDM (1:1) | 5.3 | 98.2 | 18.3 |
| KSFM-P-P/IMDM (1:2) | 5.6 | 97.3 | 18.1 |
| KSFM-P-P/IMDM (1:3) | 4.2 | 96.5 | 18.4 |
| KSFM-P-P/IMDM (2:1) | 3.53 | 97.5 | 16.4 |
| KSFM-P-P/IMDM (3:1) | 3.73 | 97.8 | 16.4 |

3. F12 mixed mediums

| P4 | Number of cells ($\times 10^6$) | Survival Rate (%) | Size (μm) |
|---|---|---|---|
| KSFM-P | 2.3 | 95.8 | 14.6 |
| F12 | 0.9 | 89.2 | 17.5 |
| KSFM-P + F12 (1:1) | 3 | 96.9 | 16.7 |
| KSFM-P + F12 (1:2) | 3.6 | 93.7 | 16.7 |
| KSFM-P + F12 (1:3) | 3.6 | 95.1 | 17 |
| KSFM-P + F12 (2:1) | 3.4 | 94.9 | 14.6 |
| KSFM-P + F12 (2:1) | 3.9 | 95.1 | 14.9 |

| P5 | Number of cells ($\times 10^6$) | Survival Rate (%) | Size (μm) |
|---|---|---|---|
| KSFM-P | 1.5 | 93.4 | 16.8 |
| F12 | 0.17 | 80.8 | 17.2 |
| KSFM-P + F12 (1:1) | 2.46 | 91.9 | 17.2 |
| KSFM-P + F12 (1:2) | 3.3 | 92.8 | 17 |
| KSFM-P + F12 (1:3) | 2.47 | 90.7 | 16.5 |
| KSFM-P + F12 (2:1) | 2.77 | 92.7 | 17 |
| KSFM-P + F12 (2:1) | 3.7 | 94.5 | 17.4 |

4. DMEM/F12 mixed mediums

| P4 | Number of cells ($\times 10^6$) | Survival Rate (%) | Size (μm) |
|---|---|---|---|
| KSFM-P | 2.1 | 94.8 | 15.2 |
| DMEM/F12 | 0.38 | 85.7 | 21.6 |

TABLE 4-continued

| | Number of cells (×10^6) | Survival Rate (%) | Size (μm) |
|---|---|---|---|
| KSFM-P + DMEM/F12 (1:1) | 4.4 | 96 | 16.3 |
| KSFM-P + DMEM/F12 (1:2) | 4.2 | 96.6 | 16.5 |
| KSFM-P + DMEM/F12 (1:3) | 3.2 | 95.8 | 16.3 |
| KSFM-P + DMEM/F12 (2:1) | 3.4 | 96 | 16.1 |
| KSFM-P + DMEM/F12 (2:1) | 3.3 | 95.9 | 16.1 |

| P5 | Number of cells (×10^6) | Survival Rate (%) | Size (μm) |
|---|---|---|---|
| KSFM-P | 1.6 | 93.3 | 16.5 |
| DMEM/F12 | 0.81 | 94.6 | 18 |
| KSFM-P + DMEM/F12 (1:1) | 2.6 | 94.5 | 17.2 |
| KSFM-P + DMEM/F12 (1:2) | 3.2 | 94.5 | 16.8 |
| KSFM-P + DMEM/F12 (1:3) | 3.8 | 96.6 | 16.8 |
| KSFM-P + DMEM/F12 (2:1) | 2.7 | 95.2 | 17.2 |
| KSFM-P + DMEM/F12 (2:1) | 4.1 | 95.4 | 16.9 |

(3) Expression of Surface Markers of Stem Cells

The adipose-derived mesenchymal cells were cultured for 5 days in each medium, and then the stem cells were collected using TriPLE solution. Then, they were dyed with each surface marker antibody (negative marker, CD31, CD34, CD45; positive marker, CD90, CD105, CD166). The surface antibody was labeled with FITC conjugated secondary antibody, and the distribution of the cells expressing the surface antibody was measured using FACs instrument.

Figure 13:
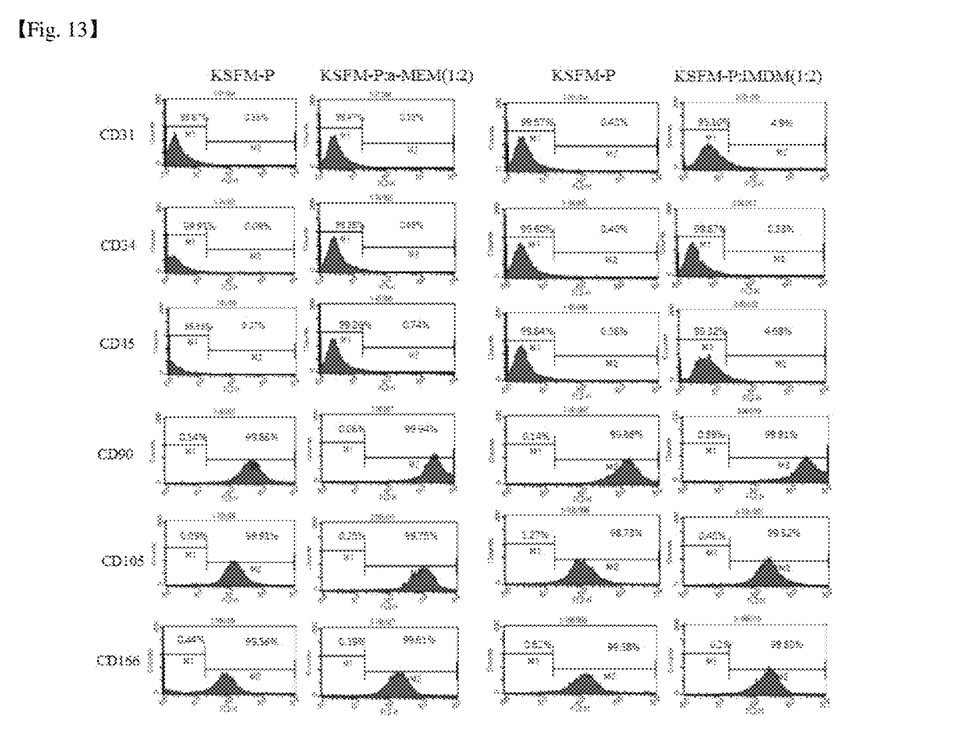
FIG. 13 illustrates the results of confirming the expression of stem cell surface markers in a mixed medium.
Figure 14:
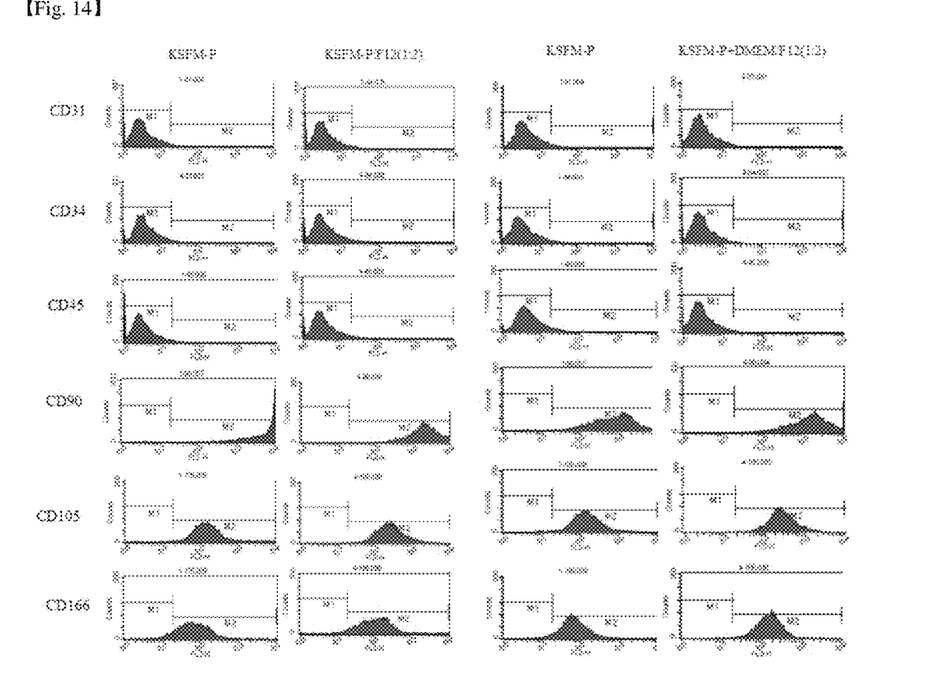
FIG. 14 illustrates the results of confirming the expression of stem cell surface markers in a mixed medium.

As a result, as shown in FIG. 13 and FIG. 14, the distribution of stem cells expressing the stem cell-specific surface markers expressed by the stem cells cultured in the KSFM-P medium mostly show the expression distribution of 0.5% or less for the negative markers CD31, CD34, and CD45, whereas the expression distribution of CD90, CD105, and CD166, the stem cell positive markers, was mostly found to be 99% or higher.

In addition, even under each of the mixed conditions (representatively 1:2 mixing), CD31, CD34, and CD45, which are negative markers of stem cell expressing stem cell-specific surface markers similar to the stem cells cultured in KSFM-P medium, were 0.5% or less. And it was confirmed that the positive markers CD90, CD105, and CD166 were also found to be 99% or higher. In other words, the culturing conditions in each mixed medium did not affect the expression of specific surface markers of stem cells, and did not affect the differentiation or characteristics of stem cells.

INDUSTRIAL APPLICABILITY

According to the present disclosure, it is possible to improve proliferation ability and differentiation ability of the mesenchymal stem cells, and is capable of producing cell therapy products more economically using the mesenchymal stem cells by enabling the mesenchymal stem cells to be cultured at a low price compared to existing culturing methods, while maintaining stem cell function.

As discussed above, the specific portions of the contents of the present disclosure have been described in detail. Therefore, it is apparent to a person having ordinary skill in the pertinent art that such specific technology is merely a preferable embodiment, and the scope of the present disclosure is not limited thereto. Accordingly, the substantial scope of the present disclosure is defined by the appended claims and their equivalents.

What is claimed is:

1. A medium composition for culturing adipose-derived mesenchymal stem cells, which comprises: a mixed medium, L-ascorbic acid 2-phosphate, fetal bovine serum, basic fibroblast growth factors (b-FGF), insulin, N-acetyl-L-cysteine, calcium chloride, and hydrocortisone, wherein the mixed medium is a mixture of Defined Keratinocyte-SFM and a medium selected from the group consisting of, α-MEM (Alpha Modification of Eagle's Medium), IMDM (Iscove's Modified Dulbecco's Medium), F12 (Nutrient Mixture F-12), and DMEM/F12 (Dulbecco's Modified Eagle's Medium; Nutrient Mixture F-12).

2. The medium composition of claim 1, wherein the medium composition contains 0.05 to 1 mM of ascorbic acid 2-phosphate, 2 to 20% fetal bovine serum, 10 to 1 ng/ml of basic fibroblast growth factor (b-FGF), 0.1 to 100 μg/ml of insulin, 0.2 to 20 mM N-acetyl-L-cysteine, 0.01 to 1 mM of calcium chloride and 5 ng/ml to 1 μg/ml of hydrocortisone.

3. The medium composition of claim 1, wherein the mixture ratio of the mediums selected from the group consisting of IMDM, α-MEM, F12, and DMEM/F12 to Defined Keratinocyte-SFM medium is 1:0.1 to 1:10.

4. The medium composition of claim 3, wherein the mixture ratio is 1:0.25 to about 1:3.

5. A method for culturing adipose-derived mesenchymal stem cells, the method comprising culturing the adipose-derived mesenchymal stem cells in the medium composition of claim 1.

6. The method of claim 5, wherein the medium composition contains 0.05 to 1 mM of ascorbic acid 2-phosphate, 2 to 20% fetal bovine serum, 10 to 1 ng/ml of basic fibroblast growth factor (b-FGF), 0.1 to 100 μg/ml of insulin, 0.2 to 20 mM N-acetyl-L-cysteine, 0.01 to 1 mM of calcium chloride and 5 ng/ml to 1 μg/ml of hydrocortisone.

7. The method of claim 5, wherein the mixture ratio of the mediums selected from the group consisting of IMDM, α-MEM, F12, and DMEM/F12 to Defined Keratinocyte-SFM medium is 1:0.1 to 1:10.

8. The method of claim 7, wherein the mixture ratio is 1:0.25 to about 1:3.

* * * * *